(12) United States Patent
Riedel et al.

(10) Patent No.: US 12,329,945 B2
(45) Date of Patent: Jun. 17, 2025

(54) DOSE RECORDING DEVICE

(71) Applicant: SANOFI, Paris (FR)

(72) Inventors: Stephan Riedel, Frankfurt am Main (DE); Matthias Felber, Will (CH)

(73) Assignee: SANOFI, Paris (FR)

(*) Notice: Subject to any disclaimer, the term of this patent is extended or adjusted under 35 U.S.C. 154(b) by 692 days.

(21) Appl. No.: 16/772,872

(22) PCT Filed: Dec. 17, 2018

(86) PCT No.: PCT/EP2018/085113
§ 371 (c)(1),
(2) Date: Jun. 15, 2020

(87) PCT Pub. No.: WO2019/121449
PCT Pub. Date: Jun. 27, 2019

(65) Prior Publication Data
US 2021/0162135 A1 Jun. 3, 2021

(30) Foreign Application Priority Data
Dec. 18, 2017 (EP) .................................. 17306806

(51) Int. Cl.
*A61M 5/315* (2006.01)
(52) U.S. Cl.
CPC .... *A61M 5/31568* (2013.01); *A61M 5/31551* (2013.01); *A61M 2205/3306* (2013.01);
(Continued)
(58) Field of Classification Search
CPC .......... A61M 5/31568; A61M 5/31551; A61M 5/31585; A61M 5/20; A61M 2205/3306;
(Continued)

(56) References Cited

U.S. PATENT DOCUMENTS

2014/0194825 A1 7/2014 Nielsen et al.
2014/0194829 A1 7/2014 Baek et al.
(Continued)

FOREIGN PATENT DOCUMENTS

CN 1099301 A 3/1995
CN 101641126 A 2/2010
(Continued)

OTHER PUBLICATIONS

PCT International Preliminary Report on Patentability in International Application No. PCT/EP2018/085113, dated Jun. 23, 2020, 7 pages.
(Continued)

*Primary Examiner* — Scott J Medway
*Assistant Examiner* — Anh Bui
(74) *Attorney, Agent, or Firm* — Bond, Schoeneck & King, PLLC (57) ABSTRACT

A dose recording device for a drug delivery device, wherein the drug delivery device comprises a housing, a cartridge holder configured to receive a cartridge for holding a plurality of doses of a drug, and a dose setting member connected to the housing and configured to set the dose of the drug, is disclosed. The dose recording device comprises a device housing and a measurement system having an optical sensor connected to a portion of the device housing. The device housing is configured to be mounted to the dose setting member. The measurement system is configured to detect a relative movement of the device housing to the housing by means of the optical sensor and to store relative movement data so as to provide information on a delivery of the dose of the drug.

21 Claims, 2 Drawing Sheets

(52) U.S. Cl.
CPC ............... *A61M 2205/332* (2013.01); *A61M 2205/3576* (2013.01); *A61M 2205/8206* (2013.01)

(58) Field of Classification Search
CPC .... A61M 2205/332; A61M 2205/3576; A61M 2205/8206; A61M 2205/52
See application file for complete search history.

(56) References Cited

U.S. PATENT DOCUMENTS

| | | |
|---|---|---|
| 2015/0018775 A1 | 1/2015 | Groeschke et al. |
| 2015/0343152 A1 | 12/2015 | Butler et al. |
| 2016/0051764 A1 | 2/2016 | Dreier et al. |
| 2017/0189625 A1* | 7/2017 | Cirillo ................. A61M 5/3155 |
| 2017/0338864 A1 | 11/2017 | Rolsted et al. |
| 2020/0206431 A1* | 7/2020 | Antonelli ................. A61M 5/24 |
| 2021/0330891 A1* | 10/2021 | Byerly .................... A61M 5/20 |

FOREIGN PATENT DOCUMENTS

| | | | |
|---|---|---|---|
| CN | 102413759 A | 4/2012 | |
| CN | 103702699 A | 4/2014 | |
| CN | 10420315 A | 12/2014 | |
| CN | 104519931 A | 4/2015 | |
| CN | 106456884 A | 2/2017 | |
| CN | 109069746 A | 12/2018 | |
| EP | 3184137 | 6/2017 | |
| JP | 2012-519027 | 8/2012 | |
| JP | 2014-516599 | 7/2014 | |
| JP | 2015-506771 | 3/2015 | |
| WO | 2009062675 A1 | 5/2009 | |
| WO | WO 2010/098929 | 9/2010 | |
| WO | WO-2010098929 A1 * | 9/2010 | ............ A61M 5/178 |
| WO | WO 2012/127046 | 9/2012 | |
| WO | WO 2013/120778 | 8/2013 | |
| WO | 2017186841 A1 | 11/2017 | |

OTHER PUBLICATIONS

PCT International Search Report and Written Opinion in Application No. PCT/EP2018/085113, dated Feb. 27, 2019, 11 pages.
First Office Action and Search Report, Chinese Patent Application No. 201880089112.5, dated Aug. 26, 2024, pp. 1-17 (with pp. 11-17 being an English translation).
Search Report (English Translation), Chinese Patent Application No. 201880089112.5, dated Feb. 26, 2025, pp. 1-2.

* cited by examiner

DOSE RECORDING DEVICE

CROSS REFERENCE TO RELATED APPLICATIONS

The present application is the national stage entry of International Patent Application No. PCT/EP2018/085113, filed on Dec. 17, 2018, and claims priority to Application No. EP 17306806.5, filed on Dec. 18, 2017, the disclosures of which are incorporated herein by reference.

TECHNICAL FIELD

The present disclosure relates to a dose recording device.

BACKGROUND

Many liquids such as medicaments have to be injected into the body. This applies in particular to medicaments, which are deactivated or have their efficiency remarkably decreased by oral administration, e.g. proteins (such as insulin, growth hormones, interferons), carbohydrates (e.g. heparin), antibodies and the majority of vaccines. Such medicaments are predominantly injected by means of delivery devices such as syringes, medicament pens or medicament pumps.

The user of such syringes, medicament pens or medicament pumps can range from healthcare professionals to the medicament-recipient themselves, the latter ranging from children or elderly persons. The medicinal injections may include repetitive or multiple injections of a particular dose (e.g. a vaccine in multi-dosage regimen) to a single injection of a single dose (e.g. a vaccine or in an emergency hydrocortisone).

For this purpose, there are several types of medication delivery devices known such as pen type delivery devices. With these delivery devices it is possible to inject several doses of the liquid from a single cartridge input into the delivery device. For different reasons, it is necessary to obtain information on the delivered doses such as the point of time and dosage of the last injection.

Despite the advantages provided by these delivery devices, there are still some drawbacks. The measurement system is integrated in the pen type injector delivery device which makes access to the system such as for replacement or maintenance purposes complicated.

Further, as the measurement system detects only the dialing operation. Thus, the measurement system does not obtain any information on an injection operation caused by an axial movement of the dose selector.

SUMMARY

Disclosed herein are a dose recording device and a delivery device allowing to obtain information not only on the dialing operation but at least additionally on the injection operation.

Embodiments of the disclosed recording device and delivery device have the features of the independent claims. Particular embodiments, which might be realized in an isolated fashion or in any arbitrary combination, are listed in the dependent claims.

As used in the following, the terms "have", "comprise" or "include" or any arbitrary grammatical variations thereof are used in a non-exclusive way. Thus, these terms may both refer to a situation in which, besides the feature introduced by these terms, no further features are present in the entity described in this context and to a situation in which one or more further features are present. As an example, the expressions "A has B", "A comprises B" and "A includes B" may both refer to a situation in which, besides B, no other element is present in A (i.e. a situation in which A solely and exclusively consists of B) and to a situation in which, besides B, one or more further elements are present in entity A, such as element C, elements C and D or even further elements.

Further, it shall be noted that the terms "at least one", "one or more" or similar expressions indicating that a feature or element may be present once or more than once typically will be used only once when introducing the respective feature or element. In the following, in most cases, when referring to the respective feature or element, the expressions "at least one" or "one or more" will not be repeated, non-withstanding the fact that the respective feature or element may be present once or more than once.

Further, as used in the following, the terms "particularly", "more particularly", "specifically", "more specifically" or similar terms are used in conjunction with optional features, without restricting alternative possibilities. Thus, features introduced by these terms are optional features and are not intended to restrict the scope of the claims in any way. The techniques described in this disclosure may, as the skilled person will recognize, be performed by using alternative features. Similarly, features introduced by "in an embodiment" or similar expressions are intended to be optional features, without any restriction regarding alternative embodiments, without any restrictions regarding the scope of the disclosure and without any restriction regarding the possibility of combining the features introduced in such way with other optional or non-optional features.

The disclosed dose recording device is configured to be used in connection with a drug delivery device, wherein the drug delivery device comprises a housing, a cartridge holder configured to receive a cartridge for holding a plurality of doses of a drug, and a dose setting member connected to the housing and configured to set the dose of the drug. The dose recording device comprises a device housing and a measurement system having an optical sensor connected to a portion of the device housing. The device housing is configured to be mounted to the dose setting member. The measurement system is configured to detect a relative movement of the device housing to the housing by means of the optical sensor and to store relative movement data so as to provide information on a delivery of the dose of the drug.

Thus, an external dose recording device is disclosed that is configured to be mounted on an existing pen type drug delivery device. The advantage of this dose recording device is that the measurement system is able to differentiate between dialing and injection. Further, the dose recording device does not require any movable parts.

The term "drug delivery device" as used herein refers to any device configured to deliver or administer a liquid from a respective cartridge. Particularly, the drug delivery device is configured to deliver or administer a predetermined dose of a liquid drug. The term "drug delivery device" shall encompass any type of device or system configured to dispense a volume of a drug into a human or animal body. The volume can typically range from about 0.5 ml to about 10 ml. Without limitation, the drug delivery device may include a syringe, needle safety system, pen injector, auto injector, large-volume device (LVD), pump, perfusion system, or other device configured for subcutaneous, intramuscular, or intravascular delivery of the drug. Such devices often include a needle, wherein the needle can include a small gauge needle (e.g., greater than about 24 gauge, and including 27, 29, or 31 gauge).

The term "liquid" as used herein refers to any liquid which is provided in single dose drug cartridge. The liquid may be a medical liquid or a dietary supplement such as a vitamin solution.

The term "drug", as used herein refers to a pharmaceutical formulation containing at least one pharmaceutically active compound. The terms "drug" or "medicament" are used herein to describe one or more pharmaceutically active compounds. As described below, a drug or medicament can include at least one small or large molecule, or combinations thereof, in various types of formulations, for the treatment of one or more diseases. Exemplary pharmaceutically active compounds may include small molecules; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more of these drugs are also contemplated.

In combination with a specific drug, the presently described devices may also be customized in order to operate within required parameters. For example, within a certain time period (e.g., about 3 to about 20 seconds for injectors, and about 5 minutes to about 60 minutes for an LVD), with a low or minimal level of discomfort, or within certain conditions related to human factors, shelf-life, expiry, biocompatibility, environmental considerations, etc. Such variations can arise due to various factors, such as, for example, a drug ranging in viscosity from about 3 cP to about 50 cP.

The drug or medicament may be contained in a primary package or "drug container" adapted for use with a drug delivery device. The drug container may be, e.g., a cartridge, syringe, reservoir, or other vessel configured to provide a suitable chamber for storage (e.g., short- or long-term storage) of one or more pharmaceutically active compounds. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of a drug formulation (e.g., a drug and a diluent, or two different types of drugs) separately, one in each chamber. In such instances, the two chambers of the dual-chamber cartridge may be configured to allow mixing between the two or more components of the drug or medicament prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drug delivery devices and drugs described herein can be used for the treatment and/or prophylaxis of many different types of disorders. Exemplary disorders include, e.g., diabetes mellitus or complications associated with diabetes mellitus such as diabetic retinopathy, thromboembolism disorders such as deep vein or pulmonary thromboembolism. Further exemplary disorders are acute coronary syndrome (ACS), angina, myocardial infarction, cancer, macular degeneration, inflammation, hay fever, atherosclerosis and/or rheumatoid arthritis.

Exemplary drugs for the treatment and/or prophylaxis of diabetes mellitus or complications associated with diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the term "derivative" refers to any substance which is sufficiently structurally similar to the original substance so as to have substantially similar functionality or activity (e.g., therapeutic effectiveness).

Exemplary insulin analogues are Gly(A21), Arg(B31), Arg(B32) human insulin (insulin glargine); Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Exemplary insulin derivatives are, for example, B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-gamma-glutamyl)-des(B30) human insulin; B29-N-(N-lithocholyl-gamma-glutamyl)-des(B30) human insulin; B29-N-(w-carboxyheptadecanoyl)-des(B30) human insulin and B29-N-(ω-carboxyheptadecanoyl) human insulin. Exemplary GLP-1, GLP-1analogues and GLP-1 receptor agonists are, for example: Lixisenatide/AVE0010/ZP10/Lyxumia, Exenatide/Exendin-4/Byetta/Bydureon/ITCA 650/AC-2993 (a 39 amino acid peptide which is produced by the salivary glands of the Gila monster), Liraglutide/Victoza, Semaglutide, Taspoglutide, Syncria/Albiglutide, Dulaglutide, rExendin-4, CJC-1134-PC, PB-1023, TTP-054, Langlenatide/HM-11260C, CM-3, GLP-1 Eligen, ORMD-0901, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, TT-401, BHM-034. MOD-6030, CAM-2036, DA-15864, ARI-2651, ARI-2255, Exenatide-XTEN and Glucagon-Xten.

An exemplary oligonucleotide is, for example: mipomersen/Kynamro, a cholesterol-reducing antisense therapeutic for the treatment of familial hypercholesterolemia.

Exemplary DPP4 inhibitors are Vildagliptin, Sitagliptin, Denagliptin, Saxagliptin, Berberine.

Exemplary hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Exemplary polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20/Synvisc, a sodium hyaluronate.

The term "antibody", as used herein, refers to an immunoglobulin molecule or an antigen-binding portion thereof. Examples of antigen-binding portions of immunoglobulin molecules include F(ab) and F(ab')2 fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region.

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in the present disclosure include, for example, Fab fragments, F(ab')2 fragments, scFv (single-chain Fv) fragments, linear antibodies, monospecific or multispecific antibody fragments such as bispecific, trispecific, and multispecific antibodies (e.g., diabodies, triabodies, tetrabodies), minibodies, chelating recombinant antibodies, tribodies or bibodies, intrabodies, nobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Exemplary antibodies are anti PCSK-9 mAb (e.g., Alirocumab), anti IL-6 mAb (e.g., Sarilumab), and anti IL-4 mAb (e.g., Dupilumab).

The compounds described herein may be used in pharmaceutical formulations comprising (a) the compound(s) or pharmaceutically acceptable salts thereof, and (b) a pharmaceutically acceptable carrier. The compounds may also be used in pharmaceutical formulations that include one or more other active pharmaceutical ingredients or in pharmaceutical formulations in which the present compound or a pharmaceutically acceptable salt thereof is the only active ingredient. Accordingly, the pharmaceutical formulations of the present disclosure encompass any formulation made by admixing a compound described herein and a pharmaceutically acceptable carrier.

Pharmaceutically acceptable salts of any drug described herein are also contemplated for use in drug delivery devices. Pharmaceutically acceptable salts are for example acid addition salts and basic salts. Acid addition salts are e.g. HCl or HBr salts. Basic salts are e.g. salts having a cation selected from an alkali or alkaline earth metal, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are known to those of skill in the arts.

Pharmaceutically acceptable solvates are for example hydrates or alkanolates such as methanolates or ethanolates.

Those of skill in the art will understand that modifications (such as, for example, adjustments, additions, or removals) of various components of the substances, formulations, apparatuses, methods, systems, devices, and embodiments described herein may be made without departing from the full scope and spirit of the present inventive concepts, which encompass such modifications and any equivalents thereof.

The term "cartridge holder" as used herein refers to any device configured to receive a cartridge. The cartridge holder may be connectable, e.g. screwable, to the housing. The cartridge holder may be removable from the housing to enable an exchange of the cartridge. The device may, thus, be a reusable device.

The term "optical sensor" as used herein refers to any optoelectronic sensor, such as a tiny low-resolution video camera, configured to take successive images of the surface relative to which the sensor is operated and moved.

The information may include a dose amount and a time of the delivery of the dose of the drug. Thus, helpful information on the delivered drug doses may be obtained.

The portion of the device housing may be made of a transparent material. Thus, the device housing does not cover a dose display such as a dose window of the dose delivery device and a user may read the displayed dose.

The device housing may comprise a front end configured to be mounted to the dose setting member and a rear end opposite to the front end, wherein the portion is located at the front end. Thus, the measurement system is configured to be close to the dose setting member which facilitates the detection of any movement thereof.

The dose recording device may further comprise grip features located at the rear end. Thus, the user may rotate the dose recording device together with the dose setting member.

The dose recording device may further comprise a power source configured to power the measurement system. Thus, the measurement system may be powered.

The power source may be disposed within the device housing. Thus, a rather compact arrangement of the power source is provided.

The power source may be a battery or a secondary battery. Thus, well established power sources may be used with the dose recording device which decreases the manufacturing costs.

The device housing may be configured to be rotatably and axially moveable relative to the housing. Thus, the dose recording device may reliably differentiate between the dialing and injection.

The measurement system may be configured to be calibrated by means of detecting rotational and/or axial movements of the device housing. Thus, the measurement system may be calibrated in a rather simple manner.

The dose recording device may further comprise a force sensor configured to detect an axial force applied to the device housing. Thus, the detection quality may be improved.

The force sensor may be disposed between the dose setting member and the device housing. Thus, it is possible to detect the movement of the dose setting member without injection until the injection starts.

The measurement system may be configured to be calibrated by means of detecting rotational and/or axial movements of the device housing corresponding to at least two different set and delivered doses. Thus, the calibration may be made with only a few process steps.

The measurement system may be configured to wireless transfer the information on a delivery of the dose of the drug to a remote electronic device. Thus, the information may be transferred with well established means which decreases the manufacturing costs. Further, as the information may be wireless transferred, the dose recording device does not need to be connected to a further connection device such as an adapter or slot.

The device housing may be designed as a sleeve. Thus, the device housing may be mounted to the dose setting member by pressing the sleeve thereon.

The device housing may comprise a length corresponding at least to a dimension with which the dose setting member is axially extendable from the housing. Thus, the device housing is rather small or compact.

The device housing may be configured to be removably mounted to the dose setting member. Thus, the dose recording device may be easily replaced or removed from the delivery device.

The optical sensor may be configured to detect the relative movement based on an outer surface structure of the housing. Thus, the optical sensor does not require a coded surface to perform its measurements. Rather, for the optical sensor to work well, the outer surface of the housing just needs to be slightly structured, which is exactly the case for the outer surface of the pen type body of the drug delivery device.

The disclosed drug delivery device comprises a housing, a cartridge holder configured to receive a cartridge for holding a plurality of doses of a drug, a dose setting member connected to the housing and configured to set the dose of the drug, and a dose recording device as described before, wherein the device housing is mounted to the dose setting member.

The housing may comprise a non-coded outer surface facing the optical sensor. The term "non-coded" as used herein refers to a substantially homogenous surface being only slightly structured and which does not comprises a code printed or otherwise disposed thereon.

Summarizing the findings of the present disclosure, the following embodiments are preferred:

Embodiment 1: A dose recording device for a drug delivery device, wherein the drug delivery device comprises a housing, a cartridge holder configured to receive a cartridge for holding a plurality of doses of a drug, and a dose setting member connected to the housing and configured to set the dose of the drug, wherein the dose recording device comprises a device housing and a measurement system having an optical sensor connected to a portion of the device housing, wherein the device housing is configured to be mounted to the dose setting member, wherein the measurement system is configured to detect a relative movement of the device housing to the housing by means of the optical sensor and to store relative movement data so as to provide information on a delivery of the dose of the drug.

Embodiment 2: The dose recording device according to embodiment 1, wherein the information include a dose amount and a time of the delivery of the dose of the drug.

Embodiment 3: The dose recording device according to embodiment 1 or 2, wherein the portion of the device housing is made of a transparent material.

Embodiment 4: The dose recording device according to embodiment 3, wherein the device housing comprises a front end configured to be mounted to the dose setting member and a rear end opposite to the front end, wherein the portion is located at the front end.

Embodiment 5: The dose recording device according to embodiment 4, further comprising grip features located at the rear end.

Embodiment 6: The dose recording device according to any one of embodiments 1 to 5, further comprising a power source configured to power the measurement system.

Embodiment 7: The dose recording device according to embodiment 6, wherein the power source is disposed within the device housing.

Embodiment 8: The dose recording device according to embodiment 6 or 7, wherein the power source is a battery or a secondary battery.

Embodiment 9: The dose recording device according to any one of embodiments 1 to 8, wherein the device housing is configured to be rotatably and axially moveable relative to the housing.

Embodiment 10: The dose recording device according to embodiment 9, wherein the measurement system is configured to be calibrated by means of detecting rotational and/or axial movements of the device housing.

Embodiment 11: The dose recording device according to embodiment 9 or 10, further comprising a force sensor configured to detect an axial force applied to the device housing.

Embodiment 12: The dose recording device according to embodiment 11, wherein the force sensor is disposed between the dose setting member and the device housing.

Embodiment 13: The dose recording device according to any one of embodiments 10 to 12, wherein the measurement system is configured to be calibrated by means of detecting rotational and/or axial movements of the device housing corresponding to at least two different set and delivered doses.

Embodiment 14: The dose recording device according to any one of embodiments 1 to 13, wherein the measurement system is configured to wireless transfer the information on a delivery of the dose of the drug to a remote electronic device.

Embodiment 15: The dose recording device according to any one of embodiments 1 to 14, wherein the device housing is designed as a sleeve.

Embodiment 16: The dose recording device according to any one of embodiments 1 to 15, wherein the device housing comprises a length corresponding at least to a dimension with which the dose setting member is axially extendable from the housing.

Embodiment 17: The dose recording device according to any one of embodiments 1 to 16, wherein the device housing is configured to be removably mounted to the dose setting member Embodiment 18: The dose recording device according to any one of embodiments 1 to 17, wherein the optical sensor is configured to detect the relative movement based on an outer surface structure of the housing.

Embodiment 19: A drug delivery device, comprising a housing, a cartridge holder configured to receive a cartridge for holding a plurality of doses of a drug, a dose setting member connected to the housing and configured to set the dose of the drug, and dose recording device according to any one of embodiments 1 to 17, wherein the device housing is mounted to the dose setting member.

Embodiment 20: The drug delivery device according to embodiment 19, wherein the housing comprises a non-coded outer surface facing the optical sensor.

SHORT DESCRIPTION OF THE FIGURES

Further features and embodiments will be disclosed in more detail in the subsequent description of embodiments, particularly in conjunction with the dependent claims. Therein, the respective features may be realized in an isolated fashion as well as in any arbitrary feasible combination, as the skilled person will realize. The scope of this disclosure is not restricted by the embodiments. The embodiments are schematically depicted in the figures. Therein, identical reference numbers in these figures refer to identical or functionally comparable elements.

DETAILED DESCRIPTION

Figure 1:
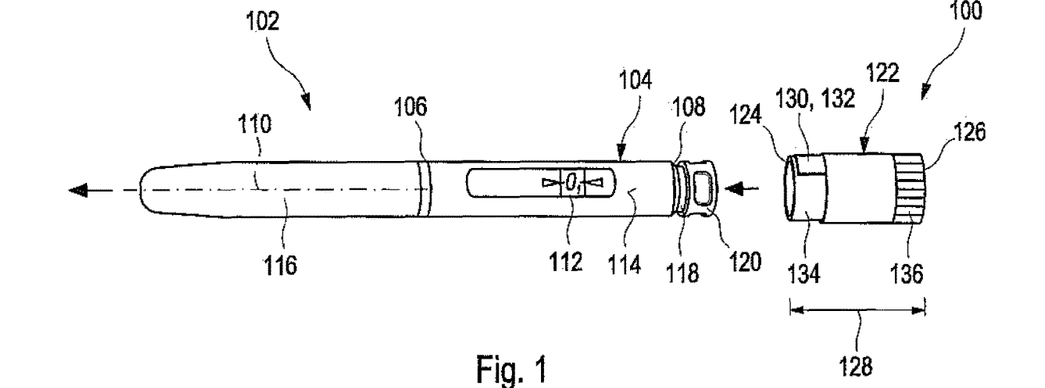
FIG. 1 shows a perspective view of a dose recording device and a drug delivery device in a disassembled state.

FIG. 1 shows a perspective view of a dose recording device 100 and a drug delivery device 102 in a disassembled state. The drug delivery device 102 comprises a housing 104. The housing 104 is adapted and arranged for protecting components of the drug delivery device 102 arranged within the housing 104 from environmental influences. The housing 104 has a distal end 106 and a proximal end 108. The term "distal end" designates that end of the housing 104 is or is to be arranged closest to a dispensing end of the drug delivery device 102. The term "proximal end" designates that end of the housing 104 which is or is to be arranged furthest away from the dispensing end of the drug delivery device 102. The distal end 106 and the proximal end 108 are spaced apart from one another in the direction of an axis 110. The axis 110 may be the longitudinal axis and/or rotational axis of the drug delivery device 102. The housing 104 comprises a dose window 112 made of a transparent material. The housing 104 comprises a non-coded outer surface 114. Thus, the outer surface 114 is merely slightly structured but does not comprise a pattern or the like printed or otherwise adhering thereon.

The drug delivery device 102 further comprises a cartridge holder 116. The cartridge holder 116 is configured to receive a cartridge (not shown in detail) for holding a plurality of doses of a drug. In the exemplary embodiment shown in FIG. 1, the cartridge holder 116 comprises a cartridge. The cartridge contains a drug, preferably a plurality of doses of the drug. The cartridge is retained within the cartridge holder 116. The cartridge holder 116 stabilizes the position of the cartridge mechanically. The cartridge holder 116 is connectable, e.g. by a threaded engagement or by a bayonet coupling, to the housing 104 at the distal end 106 thereof. The cartridge holder 116 and the housing 104 are releasably connected to one another. In an alternative embodiment, the cartridge may be directly connected to the housing 104. In this case, the cartridge holder 116 may be redundant.

The drug delivery device 102 may be a pen-type device, in particular a pen-type injector. The drug delivery device 102 may be a re-usable device, which means that the cartridge can be replaced, in particular during a reset operation, by a replacement cartridge for dispensing a plurality of doses from the replacement cartridge.

A bung (not shown in detail) is slideably retained within the cartridge. The bung seals the cartridge proximally. Movement of the bung in the distal direction with respect to the cartridge causes the drug to be dispensed from the cartridge. A needle assembly (not shown in detail) can be arranged at the distal end section of the cartridge holder 116, e.g. by means of an engagement means, e.g. a thread. A cap may be secured to the cartridge holder 116 to protect the drug delivery device 102 and, in particular, the cartridge holder 116 from environmental influences, e.g. when the drug delivery device 102 is not in use.

The drug delivery device 102 further comprises a dose setting member 118 and a dose button 120 operated for setting and dispensing a dose of the drug. The dose button 120 is located at a proximal end section of the dose setting member 118. The drug delivery device 102 comprises a piston rod (not shown in detail). The piston rod is configured to transfer movement through the housing 104 for expelling a dose of drug from the cartridge. The piston rod is moveable between an initial position with respect to the housing 104 and an end position with respect to the housing 104. The initial position may be the position of the piston rod when the drug delivery device 102 is supplied from the manufacturer. Moreover, the initial position may be the position of the piston rod after a reset operation was performed. The initial position may be the most proximal position of the piston rod. The end position may be the position of the piston rod after the complete amount of the drug was dispensed from the cartridge. The end position may be the most distal position of the piston rod. During operation of the drug delivery device 102, in particular for dispensing a dose of the drug, the piston rod is moved towards the end position.

The piston rod has a distal end, which is arranged nearest to the dispensing end of the drug delivery device 102. The distal end section of the piston rod comprises a bearing member. The bearing member is arranged between the bung and the piston rod. The bearing member is configured to reduce damages that may be caused by friction. The bearing member may be part of the piston rod. The bearing member may be connected to the piston rod. Alternatively, the bearing member and the piston rod may be integrally formed. The bearing member and the bung are in mechanical contact, in particular in abutment, throughout the operation of the device. The bearing member and the bung are in mechanical contact as long as the cartridge or a replacement cartridge is loaded within the device. In other words, the bearing member and the bung are in mechanical contact as long as the cartridge holder 116 is at least partly connected to the housing 104.

The piston rod is configured as a lead screw. The piston rod comprises two threaded sections. The threaded sections have opposite senses of rotation. A first threaded section is located at a distal part of the piston rod and a threaded section is located at a proximal part of the piston rod. The piston rod and, in particular, the first threaded section, is in threaded engagement with a guiding member (not shown in detail), e.g. a guide nut. The guiding member comprises a centered hole. Within the centered hole, a screw thread is designed. The screw thread is used for being coupled to the piston rod in order to urge the piston rod in a predetermined helical movement through the housing 104 and towards the end position. The piston rod is axially and rotationally moveable towards the end position due to mechanical cooperation with the guiding member. Furthermore, the piston rod and, in particular, the second threaded section is in threaded engagement with a drive member (not shown in detail). The drive member exerts a force onto the piston rod to cause a movement of the piston rod for delivering a dose of the drug when a user pushes onto the dose button 120. A dose set by means of the dose setting member 118 is visible through the dose window 112. For example, the number units of the drug set by the user is visible through the dose window 112.

The dose recording device 100 comprises a device housing 122. The device housing 122 is configured to be mounted to the dose setting member 118. The device housing 122 comprises a front end 124 configured to be mounted to the dose setting member 118 and a rear end 126 opposite to the front end 124. The device housing 122 is configured to be removably mounted to the dose setting member 118. The device housing 122 is designed as a sleeve. The device housing 122 comprises a length 128 corresponding at least to a dimension with which the dose setting member 118 is axially extendable from the housing 104. The device housing 122 is configured to be rotatably and axially moveable relative to the housing 104.

The dose recording device 100 further comprises a measurement system 130 having an optical sensor 132 connected to a portion 134 of the device housing 122. The portion 134 is located at the front end 124. The portion 134 of the device housing 122 is made of a transparent material. The measurement system 130 is configured to detect a relative movement of the device housing 122 to the housing 104 by means of the optical sensor 132 and to store relative movement data so as to provide information on a delivery of the dose of the drug. For this purpose, the measurement system 130 comprises a storage or memory device and an interface configured to transmit the data. The optical sensor 132 is configured to detect the relative movement based on an outer surface structure of the housing 104. Particularly, the optical sensor 132 faces the non-coded outer surface 114.

Figure 2:
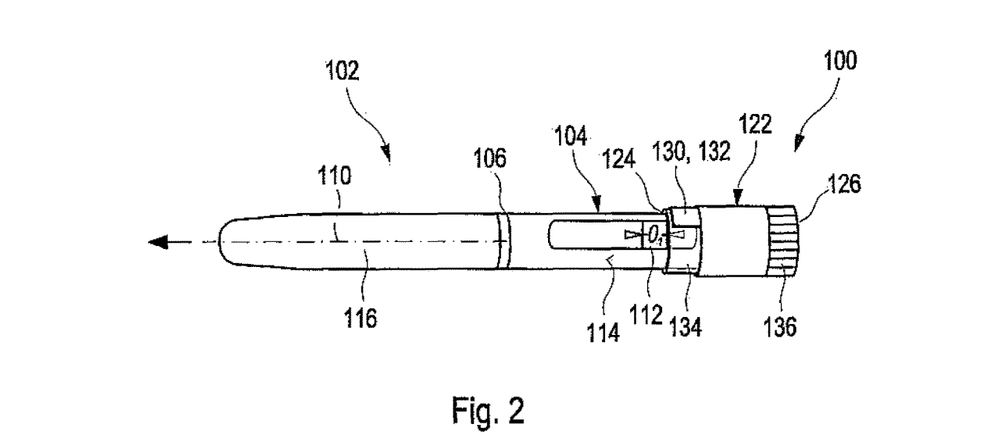
FIG. 2 shows a perspective view of the dose recording device and the drug delivery device in an assembled state.

FIG. 2 shows a perspective view of the dose recording device 100 and the drug delivery device 102 in an assembled state. The dose recording device 100 may be mounted to the dose setting member 118 by means of being pressed thereon. Thereby, the dose button 120 is disposed within the device housing 122. The dose recording device 102 further comprises grip features 136 located at the rear end 126.

Figure 3:
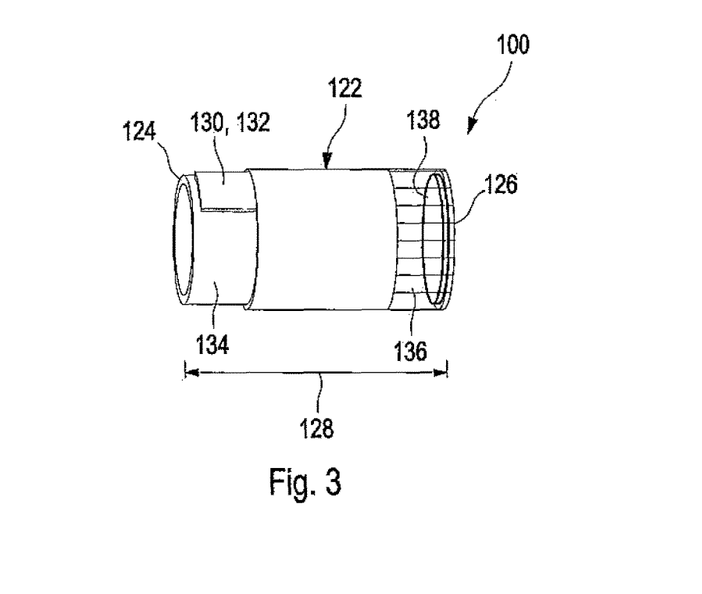
FIG. 3 shows a perspective view of the does recording device.

FIG. 3 shows a perspective view of the does recording device 100. The dose recording device 100 further comprises a power source 138 configured to power the measurement system 130. The power source 138 is disposed within the device housing 122. As shown in FIG. 3, the power source 138 is a battery. Alternatively, the power source 138 may be a secondary battery. The measurement system 130 is configured to be calibrated by means of detecting rotational and/or axial movements of the device housing 122. In the present embodiment, the measurement system 130 is configured to be calibrated by means of detecting rotational and axial movements of the device housing 122. The dose recording device 100 further comprises a force sensor (not shown in detail) configured to detect an axial force applied to the device housing 122. The force sensor is disposed between the dose setting member 118 and the device housing 122. The measurement system 130 is configured to wireless transfer the information on a delivery of the dose of the drug to a remote electronic device (not shown in detail) such as a smartphone of the user. For example, the interface may be a wireless transmission interface such as Bluetooth or WLAN.

Hereinafter, further details of the operation of the dose recording device 102 and the calibration thereof will be described below.

Figure 4:
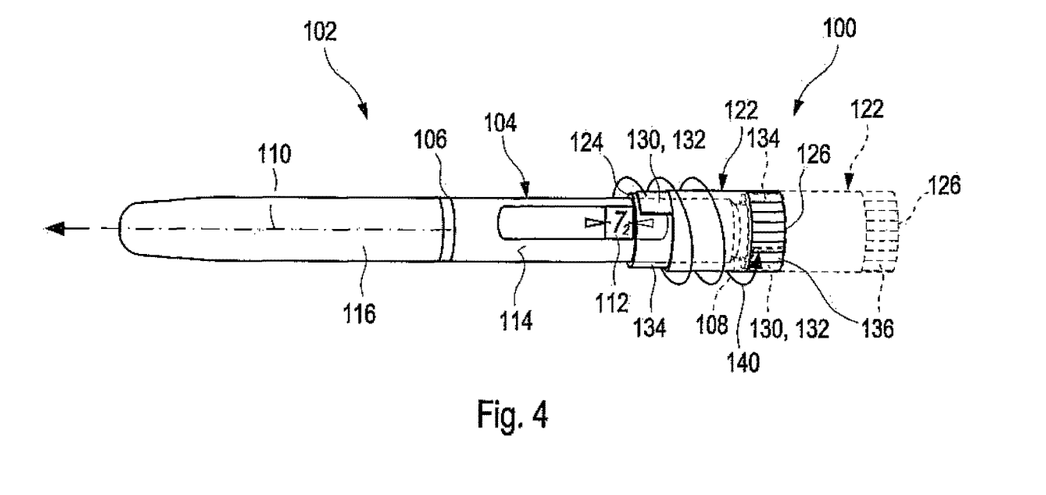
FIG. 4 shows a perspective view of the dose recording device and the drug delivery device during an operation.

FIG. 4 shows a perspective view of the dose recording device 100 and the drug delivery device 102 during an operation. For operation purpose, the dose recording device 100 is mounted to the drug delivery device 102 as described above. If the user dials a dose, he turns the dose setting member 118 by turning the device housing 122. While dialing, a helical movement indicated by arrow 140 consisting of an axial movement and a rotatory movement of the device housing 122 of the dose recording device 100 relative to the housing 104 of the drug delivery device 102 along and around axis 110, respectively, will be measured by the measuring system 130. This movement will be detected by the optical sensor 132. FIG. 4 shows the movement of the optical sensor 132 if 72 units of the drug have been dialed. Thus, the initial position for the dose recording device 100 and the position for the dose recording device 100 after dialing are shown in FIG. 4. If the user injects the drug, he presses the dose button 120 by pressing on the device housing 122. Now, the dose recording device 100 moves axially to the starting position and the measurement system 130 detects the movement corresponding to the dialed dose by means of the optical sensor 132 which monitors the outer surface 114.

It is important to detect the movement of the dose button 120 without injection until the injection starts. This can be measured with the force sensor between the dose button 120 and the device housing 122. To mount the dose recording device 100 onto the dose button 120, the user has to firmly press the dose recording device 100 on the dose button 120. This process can be used to measure the axial movement of the dose button 120 until a clutch (not shown in detail) within the housing 104 switches from dialing, i.e. rotational movement, to injection, i.e. axial movement, and thereby calibrate the measurement system 130.

Figure 5:
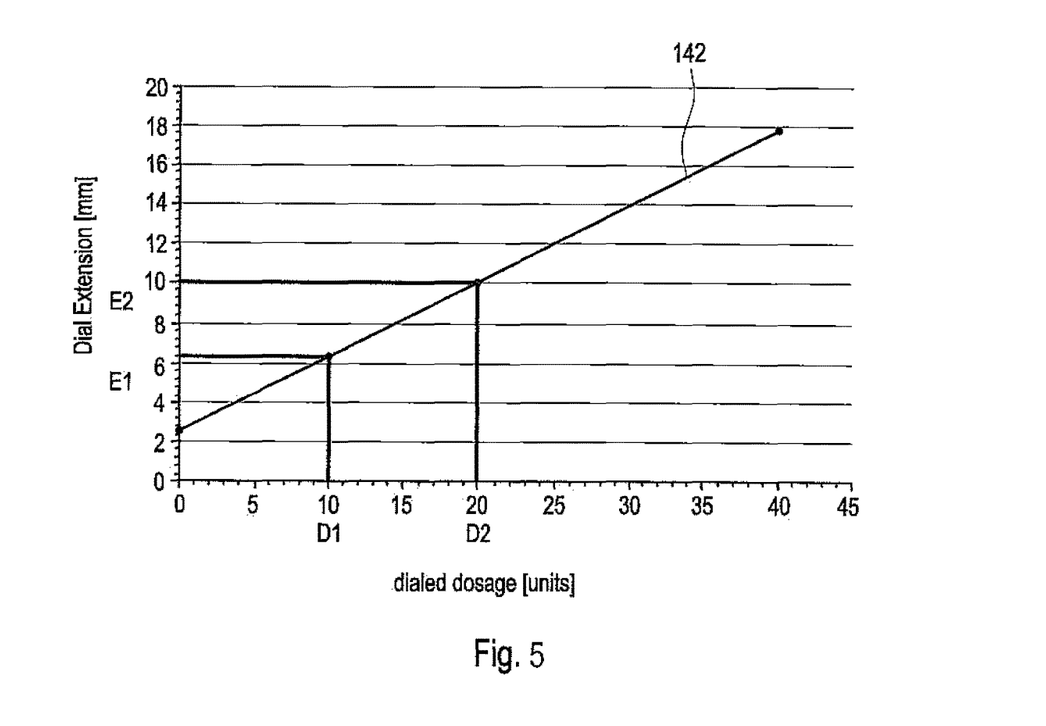
FIG. 5 shows a graph for explaining a calibration process of the does recording device.

FIG. 5 shows a graph for explaining a calibration process of the does recording device 100, which is another calibration method. The method shown in FIG. 5 is to perform a simulated injection without cartridge. The user has to dial 10 units (D1), detect a first dial extension E1 and inject. Then he has to dial 20 units (D2), detect a second dial extension E2 and inject. With the axial movement of the dose button 120, the "offset" of the dose button 120 can be calculated as offset=(E1D2-E2D1)/(D1-D2) as can be taken from the resulting calibration curve 142.

LIST OF REFERENCE NUMBERS

100 dose recording device
102 drug delivery device
104 housing
106 distal end
108 proximal end
110 axis 112 dose window
114 outer surface
116 cartridge holder
118 dose setting member
120 dose button
122 device housing
124 front end
126 rear end
128 length
130 measurement system
132 optical sensor
134 portion
136 grip features
138 power source
140 arrow
142 calibration curve

The invention claimed is:

1. A dose recording device for a drug delivery device, the drug delivery device comprising a housing, a cartridge holder configured to receive a cartridge for holding a plurality of doses of a drug, and a dose setting member connected to the housing and configured to set a dose of the drug, the dose recording device comprising:
a device housing defining a longitudinal axial direction; and
a measurement system having an optical sensor rotationally fixed to a portion of the device housing;
wherein the device housing is configured to be mounted directly to the dose setting member and is configured to rotationally fix to the dose setting member when mounted to the dose setting member; and
wherein the optical sensor is configured to detect an outer surface structure of the housing of the drug delivery device moving relative to the device housing of the dose recording device to generate relative movement data and wherein the measurement system is configured to store or to process the relative movement data so as to provide information on a delivery of the dose of the drug.

2. The dose recording device according to claim 1, wherein the information includes a dose amount and a time of the delivery of the dose of the drug.

3. The dose recording device according to claim 1, wherein the portion of the device housing is made of a transparent material.

4. The dose recording device according to claim 3, wherein the portion of the device housing is located at a front axial end of the device housing.

5. The dose recording device according to claim 4, further comprising grip features located at a rear longitudinal axial end of the device housing.

6. The dose recording device according to claim 1, further comprising a power source configured to power the measurement system.

7. The dose recording device according to claim 6, wherein the power source is disposed within the device housing.

8. The dose recording device according to claim 6, wherein the power source comprises a battery or a secondary battery.

9. The dose recording device according to claim 1, wherein the device housing is configured to be rotatably and axially moveable relative to the housing of the drug delivery device.

10. The dose recording device according to claim 9, wherein the measurement system is configured to be calibrated by detection of rotational and/or axial movements of the device housing.

11. The dose recording device according to claim 9, further comprising a force sensor configured to detect an axial force applied to the device housing.

12. The dose recording device according to claim 11, wherein the force sensor is disposed between the dose setting member of the drug delivery device and the device housing.

13. The dose recording device according to claim 10, wherein the measurement system is configured to be calibrated by detection of rotational and axial movements of the device housing corresponding to at least two different set and delivered doses.

14. The dose recording device according to claim 1, wherein the measurement system is configured to wirelessly transfer the information on a delivery of the dose of the drug to a remote electronic device.

15. The dose recording device according to claim 1, wherein the device housing comprises a sleeve.

16. A drug delivery system, comprising:
a drug delivery device comprising:
a housing;
a cartridge holder configured to receive a cartridge for holding a plurality of doses of a drug; and
a dose setting member connected to the housing and configured to set a dose of the drug; and
a dose recording device comprising:
a device housing defining a longitudinal axial direction; and
a measurement system having an optical sensor rotationally fixed to a portion of the device housing;
wherein the device housing is configured to be mounted directly to the dose setting member and is configured to rotationally fix to the dose setting member when mounted to the dose setting member; and
wherein the optical sensor is configured to detect an outer surface structure of the housing of the drug delivery device moving relative to the device housing of the dose recording device to generate relative movement data and wherein the measurement system is configured to store or to process the relative movement data so as to provide information on a delivery of the dose of the drug.

17. The drug delivery system according to claim 16, wherein the information includes a dose amount and a time of the delivery of the dose of the drug.

18. The drug delivery system according to claim 16, wherein the portion of the device housing is made of a transparent material, and wherein the portion is located at a front longitudinal axial end of the device housing.

19. The drug delivery system according to claim 16, wherein the device housing is configured to be rotatably and axially moveable relative to the housing of the drug delivery device, wherein the dose recording device further comprises a force sensor configured to detect an axial force applied to the device housing, and wherein the force sensor is disposed between the dose setting member of the drug delivery device and the device housing.

20. The drug delivery system according to claim 16, wherein the drug delivery device further comprises the cartridge received within the cartridge holder.

21. The dose recording device according to claim 1, wherein the optical sensor is fixed to a portion of the device housing that is radially outward of the housing or the dose setting member of the drug delivery device.

\* \* \* \* \*